(12) United States Patent
Möller et al.

(10) Patent No.: US 6,917,205 B2
(45) Date of Patent: Jul. 12, 2005

(54) MICROWAVE-RESONATOR AND MEASURING DEVICE

(75) Inventors: Henning Möller, Hamburg (DE); Jörg Tobias, Drage (DE); Wolfgang Taute, Laboe (DE); Reinhard Knöchel, Elmshorn (DE)

(73) Assignee: Hauni Maschinenbau AG, Hamburg (DE)

( * ) Notice: Subject to any disclaimer, the term of this patent is extended or adjusted under 35 U.S.C. 154(b) by 0 days.

(21) Appl. No.: 10/734,175

(22) Filed: Dec. 15, 2003

(65) Prior Publication Data

US 2004/0124853 A1 Jul. 1, 2004

Related U.S. Application Data

(62) Division of application No. 10/097,120, filed on Mar. 14, 2002, now Pat. No. 6,747,460.

(30) Foreign Application Priority Data

Mar. 15, 2001 (DE) .......................................... 101 12 499
Nov. 22, 2001 (DE) .......................................... 101 57 266

(51) Int. Cl.[7] .................... G01R 27/26; G01N 27/00; G01F 1/58
(52) U.S. Cl. .................... 324/663; 324/71.4; 73/861.12
(58) Field of Search ................. 324/632–646, 324/207.23; 73/861.14, 861.15

(56) References Cited

U.S. PATENT DOCUMENTS

| | | | | |
|---|---|---|---|---|
| 3,676,773 A | * | 7/1972 | Eckhardt | .................... 324/228 |
| 3,953,796 A | | 4/1976 | Keller | |
| 4,107,599 A | | 8/1978 | Preikschat | |
| 4,127,028 A | * | 11/1978 | Cox et al. | ............... 73/861.355 |
| 4,661,773 A | * | 4/1987 | Kawakita et al. | ....... 324/207.22 |
| 4,736,635 A | * | 4/1988 | Murase | ..................... 73/861.15 |
| 5,049,812 A | | 9/1991 | Le Cleach et al. | .......... 324/717 |
| 5,194,815 A | | 3/1993 | Maeno | |
| 5,334,941 A | | 8/1994 | King | |
| 5,389,883 A | | 2/1995 | Harper | ....................... 324/636 |
| 6,163,158 A | | 12/2000 | Moeller et al. | |
| 6,204,670 B1 | | 3/2001 | Joshi | |

FOREIGN PATENT DOCUMENTS

| | | |
|---|---|---|
| DE | 43 42 288 | 6/1995 |
| DE | 197 05 260 | 8/1997 |
| DE | 1 9734978 | 2/1999 |
| DE | 198 54 550 | 5/2000 |
| DE | 19854550 | 5/2000 |
| DE | 101 00 664 | 7/2002 |
| EP | 0 468 057 | 1/1992 |
| EP | 0 665 426 | 8/1995 |
| EP | 0973025 A1 * | 3/1998 |
| EP | 0 973 025 | 1/2000 |
| GB | 1354474 | 5/1974 |
| GB | 1 526 732 | 9/1978 |
| WO | WO 00/04375 | 1/2000 |

* cited by examiner

Primary Examiner—Anjan K. Deb
(74) Attorney, Agent, or Firm—Venable LLP; Catherine M. Voorhees

(57) ABSTRACT

A resonator device for testing a material quantity in the tobacco-processing industry for existence of at least one foreign substance and/or for detecting at least one of weight, density and humidity level of the material includes a resonator housing having a through opening for the material to pass through and a testing region located inside the resonator housing to which the material can be moved at least in part. The device has at least one element that increases energy density of electromagnetic waves for increasing the energy density in at least a portion of the testing region.

7 Claims, 4 Drawing Sheets

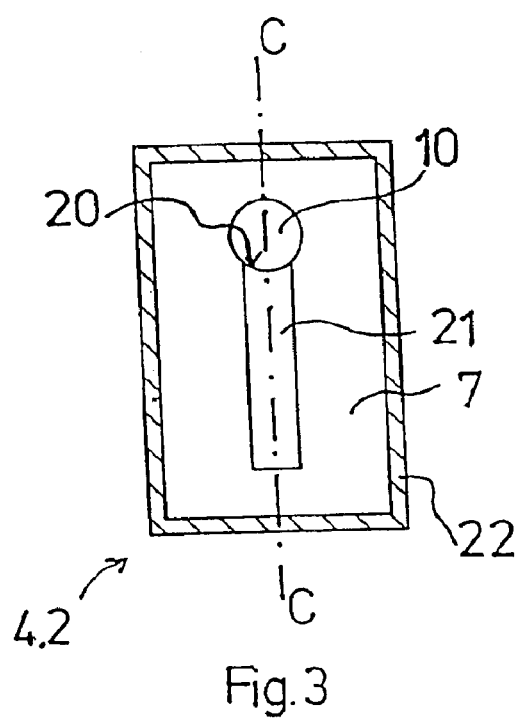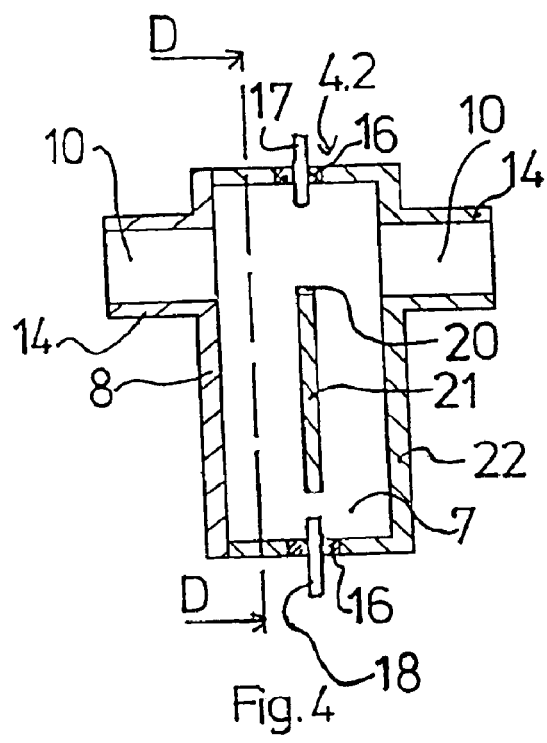

MICROWAVE-RESONATOR AND MEASURING DEVICE

CROSS-REFERENCE TO RELATED APPLICATION

This application is a divisional of U.S. patent application Ser. No. 10/097,120, filed Mar. 14, 2002 now U.S. Pat. No. 6,747,460 B2, issued Jun. 8, 2004, and incorporated herein by reference. Further, priority is claimed herein with respect to German Patent Application Serial Nos. 101 12 499.6 filed on Mar. 15, 2001 and 101 57 266.2 filed on Nov. 22, 2001, the subject matter of which, along with the subject matter of each and every U.S. and foreign patent document mentioned herein, is incorporated herein by reference.

BACKGROUND OF THE INVENTION

The invention relates to a resonator device, in particular a microwave resonator device, for testing a material quantity and especially a material flow in the tobacco-processing industry for the existence of at least one foreign substance and/or for detecting the weight, density and/or humidity level of the material or material flow. The resonator device is provided with at least one resonator housing and at least one opening in each resonator housing for the material or material flow to pass through.

The invention furthermore relates to a corresponding measuring device, especially a microwave measuring device, as well as a measuring system, in particular a microwave measuring system, for testing a material quantity and especially a material flow in the tobacco-processing industry for the existence of at least one foreign substance and/or for detecting the weight, density and/or humidity level of the material. Such a measuring device comprises at least one resonator housing, inside of which an electromagnetic field can be generated and which has at least one through opening for the material.

Finally, the invention relates to a method for testing a material for the existence of at least one foreign substance and/or for detecting the weight, density and/or humidity level of the material.

A corresponding resonator device or resonator housing for microwaves is known from German Patent No. 198 54 550 A1 commonly owned by the present assignee. This document discloses a resonator housing for the tobacco-processing industry, through which a rope of tobacco is moved and is subjected to microwaves for the purpose of detecting the weight and/or humidity level of the rope material. The purpose of this resonator housing is to improve the measuring accuracy and, if necessary, the measuring sensitivity when detecting the weight and/or humidity level of filler materials for ropes in the tobacco-processing industry. According to German Patent No. 198 54 550 A1, this is achieved by producing the housing at least in part from a material with a low expansion coefficient, so that with a corresponding fluctuation in the temperature, the housing essentially retains the same shape. It also improves the measuring accuracy if the resonator housing temperature is controlled to be at a constant value. Finally, it is advantageous according to the aforementioned reference if the interior housing walls are at least partially coated with a corrosion-resistant metal or consist of such a metal. The measuring accuracy for detecting the weight and/or humidity level for the aforementioned materials can be improved considerably in this way.

German Patent No. 101 00 664.0 also commonly owned by the present assignee, furthermore discloses a method for testing a production material or a material quantity primarily containing a production material, wherein the material is tested for the existence of a foreign substance. A microwave field is generated for this, the material is moved into the effective range of the microwave field and its influence on the microwave field is analyzed, wherein the actual values of a first and a second characteristic variable of the microwave field are measured simultaneously. A reliable value range is specified for these actual values and these are checked to determine whether the actual values are in the reliable range. A signal is generated if the actual values are outside of the reliable value range. For the purpose of this invention, the variable for a microwave field includes real variables of the generated microwave field, such as amplitude and phase, as well as variables of the components for guiding a microwave field, e.g. the resonance frequency and the band width of a resonator in which the microwave field propagates.

With the known measuring method, the goods to be measured are moved through the field of a resonator, wherein the dielectric properties of the goods to be measured change the field. By measuring the change in the resonance properties or the field, it is possible to determine the weight, density and humidity level as well as to detect foreign substances. However, it is difficult to detect very small foreign substances or to achieve a relatively exact local resolution. In particular the position of the foreign substance relative to the field orientation determines the measuring accuracy.

SUMMARY OF THE INVENTION

It is an object of the present invention to provide a resonator device, a measuring device and a measuring system, which increase the sensitivity of a method for determining whether a material flow contains a foreign substance and/or for detecting the weight, density and/or humidity level of the material flow or the material quantity.

Furthermore, it is an object of the present invention to increase the sensitivity of such a method and, in addition, provide means and a method for improving the accuracy and the local resolution of respective measurements.

The above and other objects are solved with a resonator device, in particular a microwave resonator for testing a material, in particular a material flow, in the tobacco-processing industry for the existence of at least one foreign substance and/or for detecting the weight, density and/or humidity level of the material or the material flow. The resonator device comprises a housing provided with an opening for the material quantity or the material flow to pass through, wherein the material can be transferred at least in part to a testing area, located in particular inside the resonator. At least one element that increases the energy density of electromagnetic waves is provided, wherein the energy density can be increased at least in a portion of the testing area.

As a result of this measure, a kind of bundling of the electromagnetic waves is possible in the testing area, which results in an increased flow of the respective waves, in particular microwaves, through the material to be checked or the region of the material flow to be checked. As a result, the sensitivity when measuring the weight, density and/or humidity level of the material flow and/or when testing for the existence of a foreign substance is increased, without the necessity of coupling additional energy into the resonator device. For the purpose of this invention, increasing or raising the energy density of electromagnetic waves in particular also means that these waves are bundled, focused, narrowed down or compacted. The electromagnetic waves preferably are microwaves. A material is advantageously tested with the resonator device according to the invention. The material advantageously is a material flow. For the purpose of this invention, the term testing region also encompasses the term measuring region.

The element preferably comprises a line resonator with at least one end face functioning as electrode. By using a line resonator, the waves coupled into the resonator can be bundled easily and effectively, wherein the waves or the respective field in particular exit the end face in the form of a beam.

It is advantageous if a coupling-in antenna and a coupling-out antenna are provided, which are arranged symmetrically inside the resonator. The antennas are furthermore arranged near a spot on the line resonator, where the field component that induces the coupling has a high amplitude, preferably a maximum.

A particularly good coupling of the waves coupled in and out of the element occurs if the element is preferably arranged inside a resonator cavity, at a distance to the walls delimiting the cavity.

A particularly effective method for testing the material flow is possible if the at least one end face is arranged near the material flow or the material quantity or the testing region. The size of the end face preferably is smaller than the region of the material flow, located inside a testing region in the resonator, wherein a cross-sectional surface that is essentially parallel to the end face is taken into consideration. The material flow, which in this case is a tobacco flow in the tobacco-processing industry that is advantageously wrapped with a wrapping material such as paper, refers to a cigarette rope having a circular diameter of approximately 6 to 10 mm. The size of the end face, which may be rectangular, is preferably smaller than $1/10$ of the area for the material flow to be projected against one wall of the resonator device. This refers, for example, to an area ratio as shown in FIG. 2, wherein the decisive area is the cross-sectional surface of the cigarette rope inside the cavity 7, which is shown in FIG. 2.

The line resonator preferably is a metal strip or a thin metal cube with an end face in the direction of the testing region. If at least one inside wall of the resonator housing preferably serves as an electrode, particularly as a backplate electrode to the end face, the electromagnetic wave field can be generated between the end face of the metal strip and the inside wall, so that a defined, narrowly limited measuring range is provided.

Two end faces are advantageously provided, which are directed toward the testing region. A particularly preferred embodiment of the resonator device has two end faces, wherein these are arranged opposite each other to allow the material flow to move through the space between the end faces. Such an embodiment of the resonator device permits a particularly even bundling of the waves, wherein an extremely high energy density is possible. The line resonator preferably is an open ring. In addition, the two end faces preferably are essentially parallel to each other, which further increases the homogeneity of the wave field.

Extremely reliable and exact measurements are possible if the one element consists at least in part of a material with low expansion coefficient, especially with respect to temperature. A long service life is ensured for the resonator device if the at least one element furthermore is coated with a corrosion-resistant material and in particular a metal and/or consists in part of such a material.

The invention further provides for a measuring device, in particular a microwave measuring device, for testing a material, especially a material flow in the tobacco-processing industry, for the existence of at least one foreign substance and/or for detecting the weight, density and/or humidity level of the material. The invention comprises at least one resonator housing, which is provided with at least one opening for the material to flow through and inside of which an electromagnetic field can be generated. The invention is modified in that the measuring device comprises at least two resonator housings, which respectively define one measuring range, wherein each electromagnetic field respectively comprises an electric field and the fields in the respective measuring regions are oriented in different spatial directions relative to each other. The electromagnetic field in this case is preferably a microwave field, comprising a stationary microwave field in the resonator housing. According to the invention, the different directions, relative to each other, of the electrical fields permit a more exact determination of foreign substances since foreign substances not detected with the one resonator housing can be detected with a high probability with the other resonator housing. In particular this refers to foreign substances having a geometric shape that is larger in one direction than in the other direction. Having different field directions relative to each other in space means, in particular, that these fields are distinguished by different angles relative to the conveying direction.

The measuring regions preferably are positioned successively in a conveying direction of the material flow, so that a separate evaluation of the respective measurements of the material quantity in the measuring regions can take place and so that the individual measuring regions are not influenced by the adjacent measuring region.

A particularly preferred embodiment of the present invention is obtained if the electrical fields are oriented essentially orthogonal to each other. For the purpose of this invention, orthogonal means perpendicular to each other.

If one electrical field is oriented essentially in the conveying direction of the material flow and one electrical field is oriented crosswise thereto, it is possible to take a measurement in the traditional manner, for example as described in German Patent No. 198 54 550 A1, as well as take a supplemental measurement crosswise to this direction.

For the purpose of this invention, field refers in particular to an electrical field. In the case of a dynamic field, the field intensity vector represents one field direction or orientation, as for a stationary electromagnetic wave.

If three resonator housings are provided, the measuring accuracy can be increased even further. For this, the third resonator housing is preferably designed so that the electrical field is positioned essentially orthogonal to the fields inside the other two resonator housings.

The measuring device according to the invention preferably comprises a resonator device that is designed or advantageously equipped according to the invention, as described in the above. A compact design for the measuring device is obtained if a single housing comprises at least two resonator housings.

According to a further aspect of the invention, there is provided a measuring system, particularly a microwave measuring system, for testing a material flow in the tobacco-processing industry for the existence of at least one foreign substance and/or for detecting the weight, density and/or humidity level of at least a section of the material flow. The measuring system is modified in that at least two measuring devices are provided for measuring the material flow in space, in different directions relative to each other. In this case, the measuring direction must be understood to be the direction of the field that is critical for the measurement, particularly the electrical field. For this, at least one measuring device is preferably designed such that a measuring in the conveying direction of the material flow is possible. German Patent No. 198 54 550 A1 shows in this connection, a corresponding measuring device that permits a measurement in the conveying direction of the material flow. One of the resonator devices according to the invention can be used, for example, as described in the above if at least one measuring device is designed to permit a measuring crosswise to the conveying direction of the material flow.

In a preferred embodiment of the invention, three measuring devices are advantageously provided, wherein the measuring devices are designed such that the material flow can be measured in three different spatial directions, relative to each other, in particular in essentially orthogonal directions. Very exact measurements and in particular measurements with a high local resolution are possible with a measuring system of this type. It is advantageous if the measuring device, which permits a measurement crosswise to the conveying direction, is one of the resonators according to the invention and described in the above.

According to yet another aspect of the invention, there is provided a method for testing a material quantity, in particular a material flow in the tobacco-processing industry, for the existence of a foreign substance and/or for detecting the weight, density and/or humidity of the material. For this, a first electromagnetic field is generated in a first resonator and a second electromagnetic field is generated in a second resonator, the material is moved through the first and the second field and a change in at least one characteristic of the electromagnetic field is measured.

The field intensity, the frequency or the phase, for example, can represent one characteristic of an electromagnetic field. In the case of a stationary wave field, the position of the antinodes or the nodes or the resonant frequency and the amplitude can furthermore represent one characteristic of an electromagnetic field, e.g. for a resonator.

The electrical fields are preferably oriented in different directions relative to each other. It must be assumed that the E field and the H field are oriented in different directions relative to each other. An even more exact analysis of the material flow based on the foreign substances or an even more exact detection of the density, humidity level and weight of the material flow is possible if a third resonator device is provided, which generates a third electromagnetic field. The material quantity is moved through this third field, which is oriented in a different direction relative to the first and second field, and the change in at least one characteristic of the third field is measured.

The electrical fields in the respective resonators are essentially positioned orthogonal to each other.

If the measured values are evaluated to generate an ejection signal, it is possible to separate out, for example, sections of the material flow from the further processing. As a result, it is possible to avoid the production of poorly filled cigarettes or cigarettes that are too dry or are composed of a foreign substance. The measured values from the resonators are preferably correlated, so that a very exact local resolution is possible. The rejection of conveyed material can be kept as low as possible with such an exact local resolution. Combining the measuring results from the different resonators thus increases the accuracy or the local resolution of the measurements.

BRIEF DESCRIPTION OF THE DRAWINGS

The invention is explained in further detail in the following with exemplary embodiments and by referring to the drawings, wherein reference is made to the drawings for the disclosure of all details of the invention that are not explained in further detail. Shown are in:

FIG. 3 A cross section through the resonator housing according to another exemplary embodiment of the invention.

FIG. 4 A cross section through the resonator housing in FIG. 3, along the sectional line C—C, in a view from the side.

DETAILED DESCRIPTION OF THE PREFERRED EMBODIMENTS

The same reference numbers are used for the same elements in the following Figures, so that these elements are not presented anew.

Figure 1:
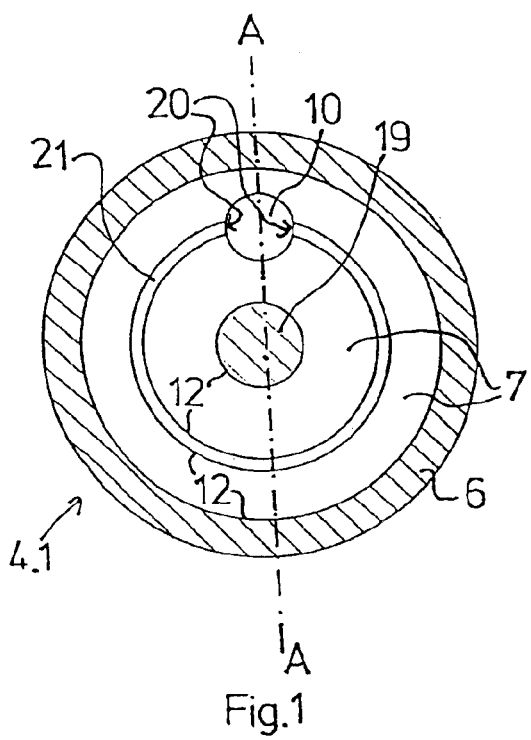
FIG. 1 A view from above of a cross section through a resonator housing.
Figure 2:
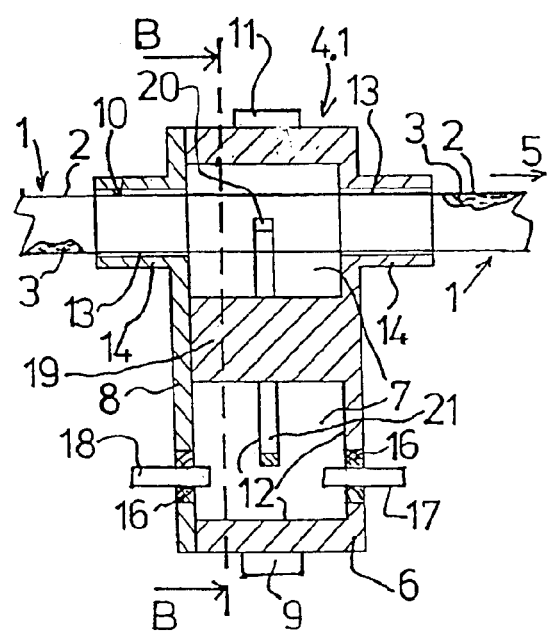
FIG. 2 A cross section through the resonator housing in FIG. 1, along the sectional line A—A.

FIG. 1 shows a view from above of a cross section through a resonator housing 4.1, wherein the view is along arrows B on the sectional line B—B in FIG. 2. Only a few of the characteristics are shown in FIG. 1. Some of the characteristics shown in FIG. 2 were not drawn into FIG. 1 for reasons of clarity. A hollow cylinder 6 of metal, preferably provided with a gold layer 12 at least on the inside, delimits the resonator housing 4.1. A post 19 is shown in the center of the hollow cylinder 6, which post is also coated with a layer of gold 12. The hollow cylinder 6 and the post 19 are shown in a cross section. One view shows a line resonator 21 in the inside space 7 or the cavity 7, which is an open ring with two end faces 20. A through bore 10 through which the cigarette rope 1 can pass is also shown.

FIG. 2 shows a partially opened up cigarette rope 1 that moves in the direction of arrow 5. The cigarette rope 1 consists of a filler material 3 of cut tobacco and a wrapper 2 of cigarette paper. The cigarette rope 1 extends through the resonator housing 4.1, to which microwave rays are fed for the purpose of detecting the weight, density and/or humidity level of the filler or for detecting the existence of a foreign substance in the filler. The resonator housing 4.1 has a cavity formed by the hollow cylinder 6, the inside space 7 of which is arranged symmetrical to the post 19. A lid 8 for closing is screwed to the hollow cylinder. The hollow cylinder 6 and the lid 8 consist of a material with very low temperature coefficient. An alloy composed at least approximately of 64% iron and 36% nickel is suitable for this. An excellent constancy of the measuring results can be achieved owing to the excellent constancy of the resonator housing 4.1 geometry. Contributing to this is also a temperature control for the resonator housing, indicated in FIG. 2, which uses a temperature sensor 9 to detect the temperature. The temperature sensor controls at least one heating transistor 11, for example a type BUZ 80 by the Siemens Company, the dissipation heat of which advantageously heats up the resonator housing, preferably via the environmental temperature. The control system itself is not shown in FIG. 2, but is known to the person skilled in the art.

A thin layer of gold 12 is deposited on the surfaces forming the boundaries of inside space 7 of resonator housing 4.1 and preferably also on the line sensor 21, which is an open ring in this case. This gold layer reliably prevents corrosion, which reduces the measuring value constancy, and simultaneously prevents a damaging side effect on the skin owing to the high electrical conductance. The resonator housing 4.1 advantageously is also gold-plated from the outside to prevent corrosion.

To prevent a soiling of the interior space 7 that would impair the measuring result, a protective tube 13 that advantageously consists of a substance of the poly aryl ether ketone (PAEK) group, e.g. poly ether aryl ketone (PAEK), is used to mechanically seal the interior space 7 against the cigarette rope 1 and any dirt particles conveyed along. The protective tube 13 can be expanded in the shape of a funnel at one of its ends, at which the rope 1 enters the resonator housing 4. For reasons of clarity this is not shown in FIG. 2.

Outside of the interior space 7, the resonator housing 4.1 extends on both sides in the shape of a tube toward the outside 14, in the direction of rope 1, so as to prevent the microwaves from exiting the resonator chamber. The tubular section can also extend to some degree toward the inside. However, this is not shown in FIG. 2.

A coupling-in antenna 17 that is insulated against the metal housing 4.1 with an insulation 16 functions to couple in the microwaves generated by the microwave generator. A coupling-out antenna 18 that is insulated against the lid 8 with an insulation 16 serves to couple out the microwaves, which are to be fed to an evaluation circuit, that is not shown herein. The aforementioned antennas 17 and 18 can also be arranged on the same housing side. In that case, they are preferably arranged offset in circumferential direction. A suitable evaluation circuit is disclosed in German Patent No. 197 34 978.1, which is thus acknowledged in this application.

The invention makes it possible to provide a directional field with increased energy density, which is particularly distinctive between the two end faces 20 or the field exit areas 20 of the line resonator 21, which is shown as an open ring for this exemplary embodiment. This results in a very short or small measuring window that clearly increases the measuring sensitivity, in particular to foreign substances.

The line resonator 21 is arranged directly adjacent to the coupling antennas 17 and 18. Non-conducting fastening means are provided for fastening the line resonator and connecting the line resonator to the housing. If a high-frequency electromagnetic alternating field emanates from the open end of the coupling-in antenna 17, a stationary wave is excited in the line resonator 21 through electrostatic induction. This wave takes energy from the coupling-in antenna 17 if the resonance condition is met, meaning if the wavelength of the stationary wave harmonizes with length L of the resonator. That is the case if the following applies: $L=n \times \lambda/2$, wherein n is a whole number. The stationary wave in the line resonator, in turn, excites through electrostatic induction an electromagnetic wave in the coupling-out antenna 18, which drains the energy from the resonator. A capacitive coupling was described in the above. However, within the framework of this invention, an inductive coupling is possible as well.

A potential antinode of the stationary wave is present at the open ends 20 of line resonator 21. The polarity of the internal surfaces is the same in this case if n is an even number and is opposite if n is an odd number. In the latter case, a concentrated electrical field is generated between the end faces, which extends through the bore for the cigarette rope. As a result, the dielectric properties of the goods to be measured exert a particularly high influence on the resonator behavior and thus lead to an effective detection of foreign substances.

FIG. 3 shows another exemplary embodiment of the present invention. In contrast to the previous embodiment shown in FIGS. 1 and 2, a hollow cube 22 is used as resonator housing 4.2 and metal strip forms the line resonator 21. FIG. 3 shows a sectional representation along the line D—D in FIG. 4, wherein this section is viewed in arrow direction. FIG. 4 is a view from the side of a sectional representation along the line C—C in FIG. 3. The additional features such as the protective tube 13, the gold layer 12, the cigarette rope 1 etc. are not shown in these Figures, so as to provide a clearer view of the elements shown.

The backplate electrode for the field exiting from the line resonator 21 or the end face 20 or from the field exit area 20 is the opposite-arranged housing wall, which functions there as ground electrode.

The exemplary embodiments according to the invention, described herein, are particularly suitable for realizing a method for testing a production material in accordance with German Patent Application 101 00 664.0. The content of this patent application is incorporated by reference into this application. The same is true for the content of the German Patent No. 198 54 550 A1 and the content of German Patent Application 197 34 978.1.

The method for testing a production material in accordance with German Patent Application 101 00 664.0 in particular is used for testing large quantities of tobacco that are automatically processed in the tobacco-processing industry, in particular to check for foreign substances that may be present in the cigarettes. These foreign substances can effect the production quality, e.g. appearance, taste and wear values. A microwave field is generated for this, the material is moved to the effective range of the microwave field and the influence of the microwave field is analyzed, wherein the actual values of a first and second characteristic variable of the microwave field are measured simultaneously. A permissible value range is specified for these actual values and a check is made to determine whether these actual values are in the permissible value range. A signal is generated in those cases where the actual values are not in the permissible value range.

The permissible value range in this case includes variable values that occur when the microwave field is influenced by a material quantity, particularly a cigarette rope that contains exclusively the production material. The material flow in this case is preferably divided into sections prior to or following the passage through the effective range of the microwave field. Sections, which generate the signal during the passage, are then removed from the material flow. The permissible value range can be determined by guiding a reference amount of the production material, which does not contain foreign substances, through the effective range of the microwave field. The actual values measured during the passage of the reference amount then form the permissible value range. The material for the reference amount can advantageously be wrapped with a wrapping material.

This process can advantageously be realized with an additional method, in which at least one characteristic of the production material is determined parallel and independent thereof from the actual values of the same characteristic variables of the microwave field. This characteristic in particular can be the density, the weight and/or the humidity level of tobacco used as production material.

Metals and plastic materials are primarily considered as foreign substances, which physically cause a totally different change in the microwave field than the water-containing tobacco material. The high conductivity of the metals causes a strong reflection or scattering of the microwaves. Plastic materials have noticeably different dielectric numbers and loss factors as compared to tobacco, so that these can also be detected easily.

With this method, different frequencies are preferably supplied to the resonator, wherein the transmission capacity for these frequencies is determined and the two variables or several characteristic variables are determined from these data with the aid of a mathematical method. Resonance curves are preferably used for this and corresponding variable pairs are determined, which are measured around a median frequency due to the insignificant detuning. Further details may be gleaned from German Patent Application 101 00 664.0.

The materials and coatings used for the exemplary embodiment according to FIGS. 3 and 4 can be the same ones used for the exemplary embodiment according to FIGS. 1 and 2.

Figure 5:
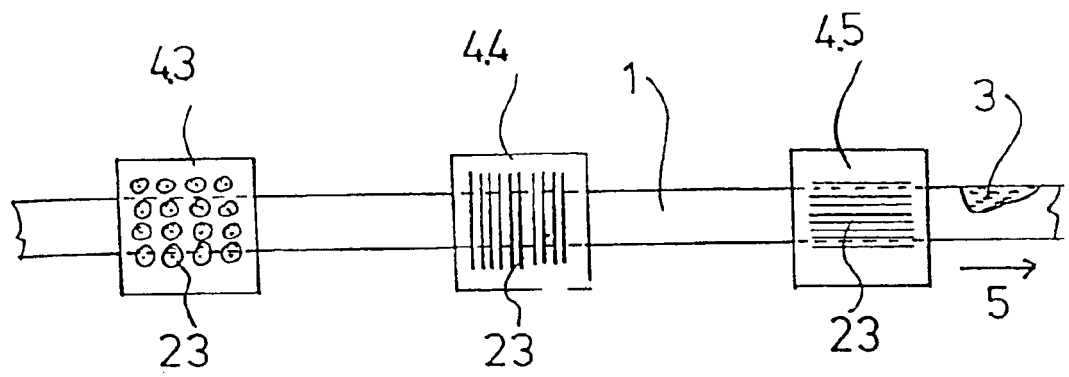
FIG. 5 A schematic of a measuring device according to the invention.
Figure 6:
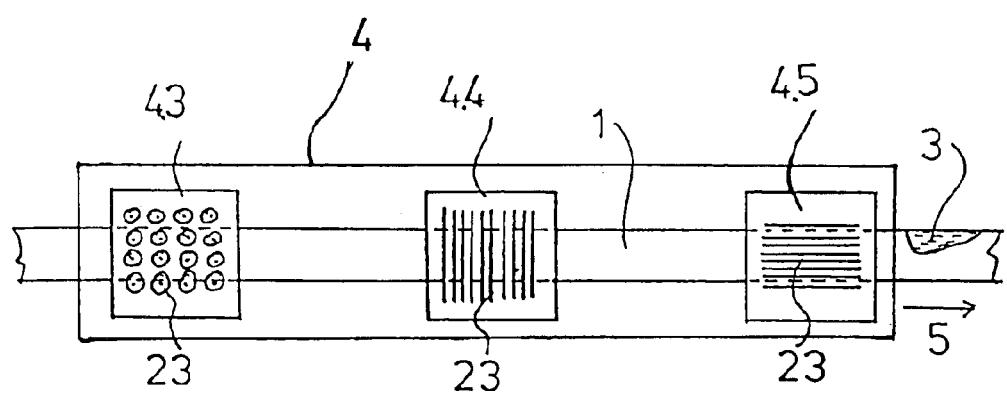
FIG. 6 A schematic of a measuring device according to another embodiment of the invention.

FIG. 5 schematically shows a measuring device according to the invention, comprising three resonators housings 4.3–4.5. A cigarette rope 1 filled with a filler 3 passes through the resonator housings 4.3–4.5. A paper strip 2 is furthermore wrapped around the filler 3. The resonator housings 4.3–4.5 contain cavities that are not shown herein. Electromagnetic fields are generated inside the cavities, which have differently oriented electrical field lines 23. Thus, the field lines 23 in the resonator housing 4.5 on the right side of FIG. 5 extend in conveying direction 5. The field lines 23 inside the resonator housing 4.4 in the center of FIG. 5 extend crosswise to the conveying direction 5, in the drawing plane, while the field lines 23 inside the resonator housing 4.3 on the left side extend crosswise to the conveying direction 5 and out of the drawing plane. In one preferred embodiment shown in FIG. 6, a single main housing 4 comprises the plurality of resonator housings 4.3–4.5.

If the field penetrates the filler 3 or rope 1 to be measured in different directions, each additional direction provides additional measuring information. Measurements are preferably taken in two or even three directions, which can be in the movement direction as well as perpendicular to it. This permits the detection of many foreign bodies, which would not be detected, for example, with a measurement exclusively in one direction.

The measuring signals can subsequently be evaluated separately, so that an ejection occurs if at least one of the sensors or measuring devices detects a foreign body. However, the measuring signals can also be linked to improve the local resolution or increase the general sensitivity of the system. The measurements are offset in time as a result of the distance between the resonator housings, the production speed or the conveying speed for material to be tested and can thus be compensated easily through calculations.

The invention has been described in detail with respect to preferred embodiments, and it will now be apparent from the foregoing to those skilled in the art, that changes and modifications may be made without departing from the invention in its broader aspects, and the invention, therefore, as defined in the appended claims, is intended to cover all such changes and modifications that fall within the true spirit of the invention.

What is claimed is:

1. A measuring system for testing a material flow in the tobacco-processing industry for existence of at least one foreign substance and/or for detecting at least one of the weight, density and humidity level in at least one region of the material flow, comprising:

a first device for measuring the material flow in a first spatial direction; and a second device for measuring the material flow in a second spatial direction that is different from the first spatial direction whereby said first device and said second device are separated from one another in a conveying direction of material flow.

2. The measuring system according to claim 1, wherein at least one of the measuring devices is arranged to make a measurement in the conveying direction of the material flow.

3. The measuring system according to claim 1, wherein at least one measuring device is arranged to make a measurement crosswise to the conveying direction of the material flow.

4. The measuring system according to claim 1, wherein the at least two measuring devices comprises three measuring devices, the third measuring device measuring the material flow in a third spatial direction that is different from the first and the second spatial directions.

5. The measuring system according to claim 4, wherein the three spatial directions are essentially orthogonal relative to each other.

6. The measuring system according to claim 1, wherein each measuring device comprises:

a resonator housing having a through opening for the material flow to pass through and a testing region located inside the resonator housing to which the material flow can be moved at least in part; and at least one element that increases energy density of electromagnetic waves for increasing the energy density in at least a portion of the testing region.

7. The measure system according to claim 1, wherein the measuring system is a microwave measuring system.

* * * * *